(12) United States Patent
Spencer et al.

(10) Patent No.: US 10,172,901 B2
(45) Date of Patent: Jan. 8, 2019

(54) POWDER FOR DELIVERY TO THE ORAL CAVITY

(71) Applicant: British American Tobacco (Investments) Limited, London (GB)

(72) Inventors: Alfred Spencer, London (GB); Andrew Frith, London (GB); Tom Woodman, London (GB); Jeremy Phillips, London (GB)

(73) Assignee: BRITISH AMERICAN TOBACCO (INVESTMENTS) LIMITED, London (GB)

( * ) Notice: Subject to any disclaimer, the term of this patent is extended or adjusted under 35 U.S.C. 154(b) by 27 days.

(21) Appl. No.: 15/318,591

(22) PCT Filed: Jun. 26, 2015

(86) PCT No.: PCT/GB2015/051870
§ 371 (c)(1),
(2) Date: Dec. 13, 2016

(87) PCT Pub. No.: WO2015/198067
PCT Pub. Date: Dec. 30, 2015

(65) Prior Publication Data
US 2017/0112889 A1    Apr. 27, 2017

(30) Foreign Application Priority Data

Jun. 27, 2014 (GB) .................................. 1411526.5

(51) Int. Cl.
| | | |
|---|---|---|
| A61K 36/81 | (2006.01) | |
| A61K 9/00 | (2006.01) | |
| A61K 9/12 | (2006.01) | |
| A61K 9/14 | (2006.01) | |
| A61K 31/465 | (2006.01) | |
| A61K 36/534 | (2006.01) | |
| A61K 47/26 | (2006.01) | |

(52) U.S. Cl.
CPC .............. *A61K 36/81* (2013.01); *A61K 9/006* (2013.01); *A61K 9/007* (2013.01); *A61K 9/0073* (2013.01); *A61K 9/12* (2013.01); *A61K 9/14* (2013.01); *A61K 31/465* (2013.01); *A61K 36/534* (2013.01); *A61K 47/26* (2013.01)

(58) Field of Classification Search
CPC .................................................... A24F 47/002
See application file for complete search history.

(56) References Cited

U.S. PATENT DOCUMENTS

| | | | | |
|---|---|---|---|---|
| 5,642,727 A * | 7/1997 | Datta | ................ | A61M 15/0045 128/202.25 |
| 2002/0062829 A1 * | 5/2002 | Ohki | ................. | A61M 15/0028 128/203.15 |
| 2004/0020503 A1 | 2/2004 | Williams | | |
| 2005/0053665 A1 | 3/2005 | Ek et al. | | |
| 2007/0267032 A1 * | 11/2007 | Shan | ..................... | A24F 47/002 131/275 |
| 2008/0138399 A1 | 6/2008 | Gonda | | |
| 2010/0170522 A1 * | 7/2010 | Sun | ........................ | A24B 13/00 131/274 |
| 2011/0011394 A1 * | 1/2011 | Edwards | ................ | A23G 1/305 128/200.18 |
| 2012/0067361 A1 | 3/2012 | Björkholm | | |
| 2012/0291780 A1 * | 11/2012 | Donovan | .......... | A61M 15/0028 128/203.15 |
| 2013/0152953 A1 | 6/2013 | Mua et al. | | |
| 2014/0017286 A1 | 1/2014 | Nilsson | | |
| 2015/0283070 A1 * | 10/2015 | Stenzler | ............... | A61K 9/0075 424/489 |
| 2017/0020183 A1 | 1/2017 | Björkholm | | |
| 2017/0112183 A1 | 4/2017 | Björkholm | | |

FOREIGN PATENT DOCUMENTS

| | | | |
|---|---|---|---|
| EP | 1 208 863 A2 | 5/2002 | |
| JP | 2002-161030 | 6/2002 | |
| WO | WO 02/038208 A3 | 5/2002 | |
| WO | WO 02/087365 A1 | 11/2002 | |
| WO | WO 2007/104573 A2 | 9/2007 | |
| WO | WO-2007117675 A2 * | 10/2007 | ............ A61M 15/06 |
| WO | WO 2010/044736 A1 | 4/2010 | |
| WO | WO 2012/134380 A1 | 10/2012 | |
| WO | WO 2014/020337 A1 | 2/2014 | |

OTHER PUBLICATIONS

PPG Silica Products, "Anti-Caking Agents", pp. 1-4, accessed at http://www.ppgsilica.com/Applications/Carrier-and-Free-Flow/Food.aspx, Jul. 15, 2017.*
Sigma-Aldrich, Particle Size Conversion Table, Chemical Technical Library, 2003-2004 (Year: 2004).*
Zoumas et al., Journal of Food Science, 45: 314-316 (Year: 1980).*
International Search Report for corresponding International Application No. PCT/GB2015/051870 dated Oct. 20, 2015; 4 pages.
Written Opinion of the International Searching Authority for corresponding International Application No. PCT/GB2015/051870 dated Oct. 20, 2015; 5 pages.

(Continued)

*Primary Examiner* — Susan T Tran

(74) *Attorney, Agent, or Firm* — Patterson Thuente Pedersen, P.A.

(57) ABSTRACT

A powder for delivery to the oral cavity of a user is disclosed. The powder includes at least two populations of particles. A first population of particles includes a stimulant, and a second population of particles includes a flavorant. Also described is a cartridge containing the powder for use in an inhaler device and inhaler device containing the powder.

15 Claims, No Drawings

(56) References Cited

OTHER PUBLICATIONS

Russian Office Action, Application No. 2016150975, dated Feb. 28, 2018, 9 pages (16 pages with translation).
Japanese Office Action, Application No. 2016-575545, dated Jan. 9, 2018, 4 pages (8 pages with translation).

* cited by examiner

POWDER FOR DELIVERY TO THE ORAL CAVITY

CROSS-REFERENCE TO RELATED APPLICATIONS

The present application is a National Phase entry of PCT Application No. PCT/GB2015/051870, filed on 26 Jun. 2015, which claims priority to GB Patent Application No. 1411526.5, filed on 27 Jun. 2014, which are hereby fully incorporated herein by reference.

TECHNICAL FIELD

The specification discloses a powder for delivery to the oral cavity of a user.

BACKGROUND

Aerosol particles may be used to deliver substances to the oral cavity of a user.

SUMMARY

In accordance with a first aspect of the present disclosure, there is provided a powder for delivery to the oral cavity of a user comprising at least two populations of particles. A first population of particles comprises a stimulant, and a second population of particles comprises a flavorant.

The powder may consist of three, four, five, or six populations of particles.

The sensations provided by the at least two populations of particles may demonstrate different rates of perception and/or duration.

The mean particle size of one of the populations of particles may be less than 50% of the mean particle size of a different population of particles. One population of particles may have a mean particle size of 7-350 µm, optionally 10-350 µm or 10-150 µm, and a different population of particles may have a mean particle size of 350-750 µm, optionally 450-750 µm.

The first population of particles may comprise a stimulant and a smaller mean particle size, and the second population of particles may comprise a flavorant and a larger mean particle size. The stimulant may be capable of being perceived quickly by the user and taking effect rapidly, and the flavorant may be capable of being perceived later and persisting for a longer duration.

At least one of the particle populations may comprise a tobacco extract.

The stimulant may comprise nicotine, caffeine, theophylline, or theobromine.

The flavorant may comprise a sugar or sugar substitute, a sensation flavorant, a saliva stimulant, and/or a sensory modifier.

At least one of the powder populations may further comprise an enhancer comprising a bioadhesive, a pH modifier, a substance capable of modifying the electrostatic charge of particles, and/or a hydrophobic material.

In some embodiments, the powder does not comprise a population of particles which consists, or consists essentially, only of sugar. In some embodiments, the powder does not comprise a population of particles which consists, or consists essentially, only of gasified sugar.

At least one of the particle populations may comprise composite particles comprising an internal core and an external coating. The coating may comprise the stimulant or flavorant.

In accordance with a second aspect of the present disclosure, there is provided a method of making a powder for delivery to the oral cavity. The method comprises separately preparing a first population of particles comprising a stimulant, and a second population of particles comprising a flavorant, and then mixing the first and second populations together.

According to a third aspect of the disclosure, there is provided a cartridge for an inhaler device, the cartridge containing a powder for delivery to the oral cavity of a user, the powder comprising at least two populations of particles, wherein a first population of particles comprises a stimulant, and a second population of particles comprises a flavorant.

According to a fourth aspect of the disclosure, there is provided an inhaler device containing a powder for delivery to the oral cavity of a user, the powder comprising at least two populations of particles, wherein a first population of particles comprises a stimulant, and a second population of particles comprises a flavorant.

In some embodiments, the inhaler of the fourth aspect may comprise a cartridge of the third aspect.

Features described in relation to the first aspect may also apply to the second, third or fourth aspects of the disclosure.

DETAILED DESCRIPTION

The disclosed powders comprise at least two populations of particles and are intended to be delivered to the oral cavity of the user in order to impart at least two different sensory experiences to the user. Specifically, the powders comprise at least a first particle population comprising a stimulant, and a second particle population comprising a flavorant.

The terms "oral cavity", "buccal cavity", and "mouth cavity" are used interchangeably and refer to the cavity lying at the upper end of the alimentary canal, bounded on the outside by the lips and inside by the oropharynx.

The particles may be delivered to the user's mouth by means of a mechanism comprising entraining the particles in a flow of air, such as that generated by user inhalation. However, the particles of the powders are not delivered to the lungs to any substantial extent. This site-specific delivery is achieved primarily as a result of the size of the particles used. The powder particles are also generally not intended for sublingual delivery to the user.

In some embodiments, the powders may comprise three, four, five, or six populations of particles. For example, the powders may consist of three, four, five, or six populations of particles. Generally, the powders consist of two populations of particles.

Particle Size

Various aspects of the sensation provided by the particle populations of the powder may be controlled as a function of the mean particle size of that particle population. For example, the magnitude, rate of onset, and duration of the sensation may all be adjusted by altering the mean particle size of that particle population.

In some embodiments, at least two of the particle populations of the powder may have different mean particle sizes. In these embodiments, the sensation associated with the particle population having a smaller mean particle size may be perceived more rapidly, but for a shorter duration, than the sensation associated with the population which has a larger mean particle size.

The mean particle size of one of the populations of particles may be substantially less than the mean particle size of a different population of particles within the powder. For example, the mean particle size of one of the populations of particles may be less than 70%, 60%, 40%, or 30% of the mean particle size of another population of particles. Generally, the mean particle size of one of the populations of particles may be less than about 50% of the mean particle size of a different population of particles within the powder.

In particular, a first population of particles may have a mean particle size of 7-350 µm, 10-350 µm, such as less than about 325, 300, 275, or 250 µm. In one embodiment, a first population of particles may have a mean particle size of less than about 150 µm.

A second population of particles may have a mean particle size of 350-750 µm, such as greater than about 375, 400, or 425 µm. In one embodiment, a second population of particles may have a mean particle size of greater than about 450 µm.

The particle size may also be important to control the delivery of the powder. For example, particles that are smaller than about 7 µm or 10 µm may be inhaled into the lower respiratory tract and airways of the lower lung. For this reason, particles of the disclosed powder are generally larger than about 7 µm or 10 µm in order to ensure that substantially all of the particles are delivered to the buccal cavity. For example, the powder particles may be larger than about 20, 30, 40, or 50 µm. Generally, in use at least 95, 98, or 99% of the particles are deposited in the oral cavity.

On the other hand, particles larger than about 750 µm may be associated with a gritty feel in the mouth which may be considered by some users to be unpleasant. For this reason, particles of the disclosed powder are generally smaller than about 750 µm and may be smaller than 720 µm, 700 µm, 650 µm, 600 µm, 550 µm or 500 µm.

Sensations

The disclosed powders comprise a first population of particles comprising a stimulant, and a second population of particles comprising a flavorant.

The sensations provided by the powder particles may be perceived by the user through various mechanisms. For example, powder components such as flavorants may be perceived directly by receptors on the tongue and the walls of the buccal cavity. Other powder components, such as stimulants, may be perceived by receptors elsewhere in the user's body after crossing the transmucosal surface.

Since the powders comprise solid particles, it will generally be necessary for the powder components to dissolve in the user's mouth before they can be perceived. In some cases, however, further reactions may be required. For example, the particles of one or more of the populations within the powder may comprise a coating which may need to dissolve in order to expose the sensation-providing component. In addition, or alternatively, it may be necessary for components of the powder to react together or to react with components of the user's saliva before the desired sensation can be perceived.

Various different types of sensation may be provided by at least two of the particle populations of the powder. For example, in some embodiments, the sensations may relate to the magnitude of the experience perceived by the user, wherein the first and second particle populations may demonstrate different rates of perception and/or duration.

In addition, or alternatively, the sensations elicited by the particle populations may relate to the provision of a sensory experience, such as a stimulant effect, flavor, and/or other sensory modification.

The rate at which the sensation provided by a population of powder particles is perceived by the user may vary considerably. For example, flavorants which are perceived by receptors in the mouth may provide the user with an essentially instant flavor sensation. Generally, rapidly perceived sensations such as these may be perceived by the user in less than 5, 3, 2, 1, or 0.5 seconds. Other sensations may be perceived significantly more slowly. For example stimulants may need to cross the transmucosal surface, accumulate in the blood, and act on receptors elsewhere in the body. Delayed sensations such as these may not be perceived by the user until at least 0.5, 1, 2, 5, or 10 minutes after powder delivery.

Moreover, the rate of perception of a sensation may be controlled and adjusted in various ways. For example, the sensation provided by smaller particles may be perceived more rapidly than that provided by a powder in the form of larger particles. In addition, the particles may be coated to delay perception of a sensation, and the solubility of the coating material may be adjusted to control the delay. In a further example, the particles may comprise an excipient, the solubility of which may regulate the release of the sensation providing component. Similar approaches may be used to control the duration over which a sensation is perceived. Generally, the user may perceive a sensation for at least 5, 10, 15, or 30 seconds.

Thus, by means of the use of a plurality of different particle populations, a powder may be produced which delivers a plurality of different sensations, wherein each sensation may be perceived with a different rate of onset, and for a different duration.

Stimulant

One or more of the particle populations within the powder comprises a stimulant.

The term "stimulant" refers to any substance that excites any bodily function, and in particular substances that stimulate the brain and central nervous system, and a substance is considered to be a stimulant if it is capable of inducing alertness, elevated mood, wakefulness, increased speech, elevated motor activity, and/or decreased appetite. Sugars, including natural sugars such as lactose, glucose and sucrose, are not stimulants.

The stimulant may, for example, comprise nicotine, caffeine, theophylline, or theobromine, and preferably consists of nicotine or caffeine. The terms "nicotine", "caffeine", "theophylline", and "theobromine" include all active forms of these compounds. The stimulant may be synthetically produced. Alternatively, the stimulant may be provided in the form of an extract from a natural source, such as tobacco, tea leaves, coffee beans, kola nuts, cocoa beans, guarana, or guayusa leaves.

In each usage of the powder, the user may consume one or a plurality of individual shots of powder. For example, in some embodiments, the powder may be packaged such that each pack contains only a single shot of powder, and in this case, the level of stimulant in the powder may be relatively high. In other embodiments, the powder may be packaged such that each pack contains multiple shots, and in this case, the powder may be arranged such that each shot contains a lower relative amount of stimulant. Thus, the amount of stimulant delivered to the user in each shot depends on the amount, frequency, and mode of delivery of the powder, wherein the powder may comprise a greater stimulant content if it is to be delivered in single shots with large intervals between shots. On the other hand, the stimulant content of the powder may be lower if a large number of shots are intended to be consumed with a high frequency. In general, when the powder comprises nicotine, the total amount of nicotine delivered in each usage of the powder may be greater than about 0.01, 0.05, 0.1, 0.2, 0.3, or 0.4 mg, and less than about 5, 4, 3, 2, or 1 mg, and may generally be, for example, between about 0.1-1.5 mg. Likewise, when the powder comprises caffeine, the intended total amount of caffeine delivered in each usage of the powder may be greater than about 10, 20, 50, 80, or 100 mg, and less than about 500, 400, 300, or 250 mg, and may generally be, for example, between about 50-400 mg.

Flavorant

One or more of the particle populations within the powder comprises a flavorant.

The terms "flavor" and "flavorant" refer to materials which, where local regulations permit, may be used to create a desired taste or aroma in a product for appropriately aged consumers. They may include for example, chocolate, coffee, wine, menthol, licorice, citrus, chamomile, fenugreek, clove, menthol, aniseed, cinnamon, cherry, berry, peach, apple, aniseed, Drambuie, bourbon, scotch, whiskey, spearmint, peppermint, lavender, honey, rose, vanilla, lemon, orange, cognac, jasmine, ginger. A single flavorant may be used, or by mixing existing flavorant, new flavors may be produced.

Generally, the flavorant may be produced from any food product, ingredient, or beverage. The flavorant may comprise imitation, synthetic or natural ingredients or blends thereof. Alternatively, the flavorant may be provided in the form of an extract from a natural source.

Thus, a single extract from a natural source, for example a tobacco extract, may comprise both a stimulant (in this example nicotine), and a flavorant (in this case tobacco-derived aromatic compounds and flavors).

One or more of the particle populations may comprise a component of tobacco, such as a tobacco extract and/or nicotine.

The flavorant may comprise a sugar and/or sugar substitute. The sugar or sugar substitute may comprise, for example, lactose, sucrose, glucose, fructose, sorbitol, or mannitol, a dihydrochalcone, monellin, a steviol glycoside, a dihydroflavonol, maltitol, sucralose, cyclamates, xylitol, a water-soluble artificial sweetener such as a soluble saccharin salt, acesulfame potassium, a dipeptide based sweetener such as an L-aspartic acid derived sweetener or aspartame, a water-soluble sweetener such as a chlorinated derivate of sucrose, for example chlorodeoxysucrose or chlorodeoxygalactosucrose; a protein based sweetener such as talin or thaumatin I or II, monatin, or a monatin derivative. In some embodiments, the flavorant may comprise saccharin.

Generally, the powder does not comprise a population of particles which does not contain a stimulant or a flavorant, and consists, or consists essentially, only of sugar. In some embodiments, the powder does not comprise a population of particles which consists, or consists essentially, only of gasified sugar.

The flavorant may comprise a sensation flavorant. The term "sensation flavorant" refers to a flavorant which provides a non-taste-specific organoleptic effect to the oral cavity. For example, a sensation flavorant may provide a drying effect, a warming or cooling sensation, or may affect the trigeminal nerve, for example by causing a tingling or fizzing sensation.

The sensation flavorant may provide a heating effect, and may for example, comprise capsaicin, dihydrocapsaicin, nordihydrocapsaicin, homodihydrocapsaicin, homocapsaicin, or nonivamide.

The sensation flavorant may provide a cooling effect, and may for example, comprise menthol or mint (for example peppermint or spearmint), cyclic alpha-keto enamines, menthyl lactate, menthone glycerine acetal, menthoxypropanediol, isopulegol, paramenthan-3,8-diol, monomenthyl succinate, monomenthyl glutarate, menthol ethylene glycol carbonate, menthol propylene glycol carbonate, 3-(1-menthoxy) propane-1,2-diol, or ethyl 3-(paramenthane-3-carboxamido) acetate.

The sensation flavorant may also function as a breath freshening agent.

The flavorant may be a sialogogue and may be capable of stimulating the flow rate of saliva. In some embodiments, the sialogogue may not have any taste or aromatic properties and may provide no other sensation in the mouth other than an increased level of saliva. The saliva stimulant may be, for example, lactose, anhydrous crystalline maltose, ascorbic acid, or malic acid.

The flavorant may be a sensory modifier. The term "sensory modifier" refers to any material which acts to flavor, enhance, or otherwise modify a subsequent or simultaneous ingestion experience by 'priming' the buccal cavity. The sensory modifier may, for example, comprise N-ethyl paramenthane 3-carboxamide.

The sensory modifier may sensorially compliment a subsequent or simultaneous smoking experience by interacting with the smoke from the smoking article. Such sensory modifiers may, for example, include glycerol, triacetin, propylene glycol or one or more long chain fatty acid.

In embodiments in which at least two of the populations of particles have different mean particle sizes, the first population of particles (having a smaller mean particle size) may comprise a stimulant, and the second population of particles (having a larger mean particle size) may comprise a flavorant. In this way, the stimulant may be perceived quickly by the user and take effect rapidly, whereas the flavorant may be perceived later and persist for a longer duration.

Enhancer

The powder may comprise a population of particles comprising an enhancer.

The term "enhancer" refers to materials which are capable of improving the delivery of the powder or a component of the powder to the user.

The enhancer may comprise a bioadhesive. The terms "bioadhesive" and "bioadhesion" refer to the state in which two materials, at least one biological in nature, are held together for an extended period of time. Thus, in this case, the inclusion of a bioadhesive may improve the bioavailability of components of the powder. Suitable bioadhesives include polyethylene glycol, polyvinyl alcohol, polyvinyl pyrrolidone, polyacrylic acid, polyhydroxyethyl methacrylate, and chitosan.

The bioadhesive may be a mucoadhesive. Mucoadhesives may be included in the powder to enable prolonged retention at the buccal mucosal surfaces. Mucoadhesives may have numerous hydrophilic groups, such as hydroxyl, carboxyl, amide, and sulfate, which attach to mucus or the cell membrane by various interactions such as hydrogen bonding and hydrophobic or electrostatic interactions. Suitable mucoadhesives include lectins and thiolated polymers.

The enhancer may comprise a pH modifier. Substances which modify the pH of particles within the powder may increase the pH of the oral cavity. The resting pH of the oral cavity is typically slightly acidic (6.4-6.9), and providing a powder comprising particles which increase the pH of the oral cavity can aid transmucosal uptake. Thus, in order to accelerate or reduce the rate of perception of a sensation, the powder may include a pH modifier such as sodium carbonate, sodium hydroxide, sodium silicate, sodium phosphates, lime, phosphoric acid, poly phosphoric acid, citric acid, potassium sorbate, poly ethylene imine (PEI).

The enhancer may comprise a substance capable of modifying the electrostatic charge of particles. Such substances may be included in order to modify the flow of particles within the powder. Charged particles tend to adhere to the walls of the device from which the powder is to be delivered, which can adversely affect the accuracy of the delivered dose. Modification of the electrostatic charge of particles within the powder, typically so that the particles repel each other, can help to prevent such adherence. Use of particular processing parameters for production of the particles can help achieve this aim. Alternatively, or in addition, one or more substances can be included in the powder which modify the electrostatic charge of the particles. For example, the powder may comprise one or more electrets.

The enhancer may comprise a hydrophobic material. Hydrophobic materials can improve mouth feel and minimize water absorption by the particles prior to use, thereby extending shelf-life, and/or extending the time over which the user perceives the sensory experiences imparted by the powder. Suitable hydrophobic materials include waxes, fatty acids or salts thereof; monoglycerides, diglycerides or triglycerides; glyceryl behenate, hydrogenated vegetable oil, stearic acid, glyceryl monostearate, glycerylpalmito stearate or cetyl alcohol.

Excipient

The powder may comprise particles of one or more excipient. The term "excipient" refers to a substantially inert material. Such materials are typically used as, for example, bulking agents, taste regulators, and/or to enhance palatability.

In addition, the presence of an excipient within the powder can contribute to, and improve, the delivery of the powder to the buccal cavity of a user. Particles within powders tend to agglomerate, and adhere to surfaces within the device which is intended to deliver the powder to the user. Small particles (less than 50 μm) in particular may be thermodynamically unstable due to their high surface area to volume ratio. This provides excess surface free energy and encourages particles to agglomerate. Agglomeration of particles and adherence of particles to the surfaces of the device can result in the particles leaving the device as large stable agglomerates or being unable to leave the device and remaining adhered to the interior of the device. Uncertainty as to the extent of formation of stable agglomerates of the particles between each actuation of the device can lead to reduced powder delivery and/or poor dose reproducibility. Inclusion of excipient particles can decrease agglomeration and adherence of particles within the powder to surfaces within the device, thus improving powder flow.

Examples of suitable excipients include sugar, starch, lactose, acacia, sodium alginate, carbomer, sodium carbonate, calcium phosphate or calcium carbonate, cellulose, ethyl cellulose, methyl cellulose and povidone.

The excipient material may be purchased from a supplier, for example Meggle®. The excipient material may be purchased in the form of particulate material, with particles within the desired size range. Alternatively, the purchased excipient material may be processed, for example to break down agglomerates and/or reduce particle size to give particles in the desired size range. The excipient particles may then be classified by size, for example by sieving, and the desired particle size fraction selected.

The powder may comprise excipient material in the form of a population of excipient particles. Such a population may comprise up to 99% by weight of the total powder. For example, the excipient particle population may comprise up to 20%, up to 30%, up to 40%, up to 50%, up to 60%, up to 70%, up to 80%, up to 90%, up to 95%, or up to 98% by weight of the total powder.

In addition, or alternatively, the powder may comprise a population of composite particles, wherein each composite particle comprises a plurality of materials that are irreversibly bound together to form a single particle. In this case, the composite particles may comprise a combination of excipient material and one or more other materials such as a flavorant, stimulant, and/or enhancer.

Particle Composition

The disclosed powder comprises at least two different populations of particles. The terms "population of particles", "particle population", and similar expressions refer to a plurality of particles having the same or substantially the same characteristics. For example, the particles within a single population have the same, or substantially the same, size, shape, composition, etc, within a limited range, for example, differing from the mean value by less than 5%, 2%, or 1%.

The powder may comprise a population of particles wherein each particle is composed of a single material. For example, each particle of the population may simply comprise particles of a flavorant or particles of a stimulant.

Alternatively, each particle within a population may have a more complex structure and/or may be composed of a plurality of materials.

For example, each particle within the population may comprise a layered composition, wherein the particle comprises an inner core and an outer coating. In this case, the core may comprise excipient material and the coating may comprise a flavorant and/or stimulant.

When the particle population comprises an enhancer, this may generally be present in an outer layer. Thus, each particle in a population may comprise a core comprising a flavorant or stimulant, and a coating comprising an enhancer.

In some embodiments, each particle within the population may comprise three or more materials, such as four, five, or six materials. For example, each particle within a population may have a multi-layered composition and may comprise a core comprising excipient material, an intermediate layer comprising a flavorant and/or stimulant, and an outer coating comprising an enhancer.

When the particle population comprises two or more flavorant, stimulants, and/or enhancers, these may be provided in the form of different layers. Alternatively, a single layer may comprise a mixture of two or more different materials such as flavorants.

Each layer or coating may be complete, that is, it may encompass the entire particle. Alternatively, the layer or coating may be incomplete, that is, it may only partially cover the particle.

By means of the use of layering in this way, a population of particles may be produced which provides more than one sensory experience to the user, wherein each sensory experience may be perceived sequentially. The use of multiple layers may also extend the time over which the user perceives a sensory experience.

In some embodiments, the powder comprises particles having one or more distinct shapes. The shape of the particles may, for example, affect the mouth feel experienced by the user, and/or the rate of dissolution of the particles in the buccal cavity. The powder may, for instance, comprise particles in the form of flakes, particles which are substantially spherical, and/or particles which are substantially rectilinear.

Different particle shapes may be achieved by means of different processing methods, for example, substantially spherical particles may be produced by spray drying.

Powder Properties

The powder may be a free-flowing powder in order that it can be readily entrained in a fluid flow for inhalation.

In some embodiments, the powder may comprise less than about 50 wt %, 40 wt %, 30 wt %, 25 wt %, 20 wt %, 15 wt %, 10 wt %, 5 wt %, 4 wt %, 3 wt %, 2 wt % or 1 wt % moisture (on a wet weight basis). High moisture levels can cause powders to agglomerate, which can reduce the amount of powder entrained in a fluid flow in use. Dry, free flowing powders are more readily entrained in a fluid flow in use, increasing the total particulate matter per puff.

Method of Production

In a second aspect, there is provided a method of making a powder according to the first aspect, as described above.

Generally, methods involve separately producing at least two different particle populations and then mixing them to form the disclosed powder. Mixing is generally performed using a relatively gentle mixing method, such as by means of a rotary mixer or a tumbler mixer.

Various suitable methods of producing particulate material will be known to the skilled person. For example, one method may involve wet mixing the ingredients using a high-shear granulator or simple planetary mixer; extruding the resultant mixture; spheronizing the extrudates; and finally drying the resultant particles, for example in a vertical fluid bed drier.

Another method may simply involve producing one or more large solid masses of the desired material; pulverizing the one or more masses; and size classifying the resultant particulate matter to obtain particles of the desired size.

Some approaches may involve creating particulate material by drying a solution or suspension. Any means of drying the solution or suspension which gives rise to a particulate material may be used. For example, the solution or suspension may be dried using means such as spray-drying, drum drying, freeze drying, crystallization, pulse-combination drying, dielectric or microwave drying or use of a fluid bed granulator.

The resultant particles may then be provided with a coating, as discussed above. The coating may be applied to the particles by spraying, dipping, or any other method of applying a coating. For example, a solution(s) of the constituent(s) to be coated onto the particles may be prepared, and then applied to the particles using fluidized bed coating; top or bottom spray coating; pan coating; air-suspension coating; or vapor coating.

In some embodiments, the particles may undergo a deagglomeration step in order to break down agglomerated particles. The deagglomeration step may involve mechanically breaking up agglomerates, for example by sieving or vibration of the particles.

Resultant particles may then be classified by size, for example by sieving, and the desired particle size fraction selected.

Tobacco Extract

As described above, the flavorant and/or stimulant may be provided in the form of a tobacco extract.

The tobacco extract may be made by any suitable method. For example, WO 2014/020337, the entirety of which is hereby expressly incorporated by reference, discloses an example of a tobacco extract which may be used in the disclosed powders.

As disclosed in WO 2014/020337, raw tobacco material may be combined with water in a mixer, such as a plough-share or drum mixer, and stirred at about 50 revolutions per minute (rpm) for about 1 hour at a defined temperature, which may be selected to minimize the loss of aromatic components and/or volatile aromatic compounds, such as nicotine, from the mixture. Accordingly, the mixing step may be carried out at or below ambient temperature (considered to be 18-25° C.). The pH of the mixture may be adjusted prior to, during and/or after the process of the production of tobacco extract, to about pH 5.5.

During and/or after the mixing of the tobacco material and water, the solid and liquid components of the mixture may be separated by any suitable apparatus, such as a hydropress, one or more centrifugation step(s) and/or a belt press.

The tobacco extract may then undergo treatment to remove microbes, for example by membrane filtration, in order to enhance safety in use.

Powder Delivery/Inhaler Device

The disclosure provides an inhaler device containing a powder as described herein. The inhaler device may comprise a housing and a powder chamber within the housing. The powder chamber may be a cartridge which is retained in the housing in use, the cartridge containing the powder. The cartridge may be removable, allowing the cartridge to be recharged or replaced once the power has been at least partially consumed. In some embodiments, the cartridge may be retained in the housing by any suitable means, such as magnetic retention. The cartridge may be retained by a screw-fit, snap-fit or bayonet-fit into the housing.

In some embodiments, the disclosure provides a cartridge containing a powder as described herein, wherein the cartridge is for use in an inhaler device as described herein. In some cases, the cartridge is adapted to be placed in an inhaler device as described herein. The cartridge may be formed using a rigid materials such as a plastics or metal material.

In some embodiments, the inhaler device may comprise a closure mechanism. This mechanism is moveable between an open configuration and a closed configuration. In the closed configuration, powder cannot exit the device. The device must be placed in the open configuration in use to allow inhalation. In some embodiments, the closure mechanism may comprise a cap or lid.

In use, the powder may be entrained in a fluid flow to create an aerosol which is then inhaled. The fluid is typically a gas, suitably air. In some embodiments, the powder is entrained in air which is drawn through the device by the user inhaling.

In some embodiments, the inhaler device may be puff actuated. In such embodiments, the device may comprise a housing which defines a fluid flow path, the path extending from an inlet provided in the housing, through a powder chamber within the housing and to an outlet from the housing. In use, the user draws air through the fluid flow path by inhaling through the flow outlet (i.e. at the downstream end of the flow path). As the air passes through the powder chamber, powder is entrained in the air flow and exits the housing at the outlet (and is thus delivered to the user).

In some embodiments, at least one one-way valve may be provided in the fluid flow path, the valve(s) being orientated such that in use, powder may only exit the housing through the outlet. The valve is biased to a closed position in the absence of a fluid flow. This arrangement minimizes or prevents powder loss through the fluid flow inlet (caused by a fluid flow in the wrong direction).

In some embodiments, one-way valves may be provided both upstream and downstream of the powder chamber, the valves being biased to a closed position in the absence of a fluid flow. The valves are directed to allow fluid flow from the inlet to the outlet only. This means that powder cannot exit the powder chamber without a fluid flow being present, minimizing or preventing loss of the powder when the device is not in use.

In alternative embodiments, the fluid flow may be created by an aerosol generating means, such as a propellant, located in the inhaler device.

In some other embodiments, the device may be push-button actuated. In some embodiments, the device may comprise aerosol generating means, wherein the powder may be entrained in a fluid flow created by the aerosol generating means. In such embodiments, the aerosol generating means may comprise an aerosol generating material or propellant which may be retained in a chamber in the inhaler device, and released by actuation of a push-button by the user.

The disclosed powders are typically delivered to the buccal cavity as one or more shots or doses. Several shots of powder may be consumed in each session of powder usage. Each shot may contain up to about 10 g of powder, such as up to about 5, 3, 2, or 1 g. Generally, each shot contains up to about 500 mg, such as between about 5-450 mg, 10-400 mg, 50-375 mg; between 100-350 mg or around 10, 20, 50, 75, 100, 150, 200, 250, 275, 300, 325, 350, 375, 400, 425, 450 or 475 mg. Generally, the amount of powder delivered per shot must be sufficient for the sensations provided by the powder populations to be perceived by the user.

EXAMPLES

A powder was produced comprising two populations of particles. Particles of the first population were prepared from a tobacco extract, containing a plurality of alkaloid stimulants including nicotine. Particles of the second population contained a flavorant in the form of mint oil.

Preparation of Tobacco Extract 12 kg of de-ionized water was added to 8 kg of tobacco material in a Winkworth RT200 mixer and the mixture was stirred at 50 rpm for 60 minutes. The solid and liquid components of the mixture were separated using a Vigo hydropress, producing raw tobacco extract and a solid extract which was discarded. All of the steps of the production of the extract were carried out at 25° C.

Treatment of Tobacco Extract to Reduce Microbial Content 6 liters of the raw tobacco extract was passed through a sieve with a mesh size of 25 μm. The filtrate was centrifuged at 8000 rpm for 10 minutes using a Beckman Avanti J-20XP centrifuge at 4° C. The liquid phase was passed through a membrane with a pore size of 10 μm (Millipore Isopore® membrane, catalogue no. TCTP04700). The filtrate was passed through a membrane with a pore size of 5 μm (Millipore Isopore® membrane, catalogue no. TMTP04700). The filtrate was centrifuged at 8000 rpm for 10 minutes using a Beckman Avanti J-20XP centrifuge at 4° C. The liquid phase was passed through a membrane with a pore size of 1.2 μm (Millipore Isopore® membrane, catalogue no. RTTP04700), the filtrate was centrifuged at 8000 rpm for 10 minutes using a Beckman Avanti J-20XP centrifuge at 4° C. and the liquid phase was passed through a membrane with a pore size of 0.45 μm (Whatman® cellulose acetate 47 mm membrane, catalogue no. 7000 0004). The filtrate from this microfiltration step was then passed through a membrane with a pore size of 0.2 μm (Whatman® cellulose acetate 47 mm membrane, catalogue no. 7001 0004). Unless stated otherwise, the steps of the extract treatment process were carried out at 25° C.

Nicotine Content of Tobacco Extract

The nicotine content of the extract was determined according to a method based on Canadian official method T-301, "Determination of Alkaloids in Whole Tobacco". The method was carried out three times and the average nicotine content was found to be 20.06 mg/mL.

Preparation of Particulate Material from Tobacco Extract

The tobacco extract was then spray dried to produce particulate material.

The resultant particles were then sieved using a 10 μm mesh sieve followed by a 150 μm mesh sieve. The particles that were retained after the first sieving step, but that passed through the sieve following the second sieving step were selected.

Production of Mint Particles

About 500 ml of boiling water was added to about 250 g of crushed mint leaves. After the mixture had been allowed to steep for 24 hours the mixture was strained and the solids discarded.

To the liquid was added the beaten white of an egg and about 900 g of sugar. The mixture was boiled slowly until thick.

Pellets were produced by dropping small spoonfuls of the mixture into cold water. When cold and dry the pellets were crushed. The resultant particles were sieved using first a 450 μm mesh sieve and then a 700 μm mesh sieve. The particles that were retained after the first sieving step, but that passed through the sieve following the second sieving step were selected.

Production of Powder

To produce the final powder, particles of the first particle population (comprising a tobacco extract), and second particle population (comprising mint particles), were mixed together using a Turbula mixer at 40 rpm for 2 hrs.

The ratio in which the two populations of particles were mixed was such that approximately 500 mg of the final powder contained about 1 mg of nicotine.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilized and modifications may be made without departing from the scope of the claimed invention. Various embodiments of the invention may suitably comprise, consist of, or consist essentially of, appropriate combinations of the disclosed elements, components, features, parts, steps, means, etc, other than those specifically described herein. In addition, this disclosure may include other inventions not presently claimed, but which may be claimed in future.

The invention claimed is:

1. An inhaler device containing a powder for delivery to the oral cavity of a user, the powder comprising at least two different populations of particles,
   wherein a first population of particles has a mean particle size of 7 μm-350 μm and comprises a stimulant comprising nicotine, and a second population of particles has a mean particle size of 350 μm-750 μm and comprises a flavorant, or wherein a first population of particles has a mean particle size of 350 μm-750 μm and comprises a stimulant comprising nicotine, and a second population of particles has a mean particle size of 7 μm-350 μm and comprises a flavorant, and wherein the powder does not comprise a population of particles that consists only of sugar.

2. The inhaler device according to claim 1, wherein the powder consists of three, four, five, or six populations of particles.

3. The inhaler device according to claim 1, wherein the stimulant sensation provided by the first population of particles demonstrates a different rate of at least one of perception or duration compared to the flavorant sensation provided by the second population of particles.

4. The inhaler device according to claim 1, wherein the mean particle size of the first population of particles is less than 50% or greater than 100% of the mean particle size of the second population of particles.

5. The inhaler device according to claim 1, wherein nicotine is an extract from tobacco.

6. The inhaler device according to claim 1, wherein the stimulant further comprises caffeine, theophylline, or theobromine.

7. The inhaler device according to claim 1, wherein the flavorant comprises at least one from the group consisting of a sugar substitute, a sensation flavorant, a saliva stimulant, and a sensory modifier.

8. The inhaler device according to claim 1, wherein at least one of the at least two different populations of particles further comprises at least one of an enhancer comprising a bioadhesive, a pH modifier, or a hydrophobic material.

9. The inhaler device according to claim 1, wherein at least one of the at least two different populations of particles is composite particles comprising an internal core and an external coating.

10. The inhaler device according to claim 9, wherein the coating comprises the stimulant or flavorant.

11. The inhaler device of claim 1, further comprising a cartridge containing the powder.

12. The inhaler device according to claim 1, wherein the mean particle size of the first population of particles is 10 μm-350 μm and the mean particular size of the second population of particles is 350 μm-750 μm, or the mean particle size of the second population of particles is 10 μm-350 μm and the mean particle size of the first population of particles is 350 μm-750 μm.

13. The inhaler device according to claim 12, wherein the mean particle size of the first population of particles is 10 μm-150 μm and the mean particle size of the second population of particles is 350 μm-750 μm, or the mean particle size of the second population of particles is 10 μm-150 μm and the mean particle size of the first population of particles is 350 μm-750 μm.

14. The inhaler device according to claim 1, wherein the mean particle size of the first population of particles is 10 μm-350 μm and the mean particle size of the second population of particles is 450 μm-750 μm, or the mean particle size of the second population of particles is 10 μm-350 μm and the mean particle size of the first population of particles is 450 μm-750 μm.

15. The inhaler device according to claim 1, wherein at least one of the first population of particles or the second population of particles further comprises one or more electrets.

* * * * *